United States Patent [19]

Hedrich et al.

[11] 4,021,225

[45] May 3, 1977

[54] COMBATING UNWANTED VEGETATION WITH 1,3,4-THIADIAZOLE-2-SULFONAMIDES

[75] Inventors: Loren W. Hedrich, Overland Park; William C. Doyle, Jr., Leawood, both of Kans.

[73] Assignee: Gulf Research & Development Company, Pittsburgh, Pa.

[22] Filed: Feb. 26, 1971

[21] Appl. No.: 119,417

[52] U.S. Cl. .................................. 71/90; 71/88; 260/239 A; 260/239 AA; 260/239 B; 260/293.85; 260/306.8 D
[51] Int. Cl.² ......................................... A01N 9/12
[58] Field of Search ................................ 71/90

[56] References Cited

UNITED STATES PATENTS

| | | | |
|---|---|---|---|
| 3,482,957 | 12/1969 | Ueno et al. | 71/103 |
| 3,657,264 | 4/1972 | Rucker et al. | 71/90 |
| 3,658,830 | 4/1972 | Pilgram et al. | 71/90 |
| 3,673,203 | 6/1972 | Miller | 71/90 |
| 3,686,198 | 8/1972 | Metzger et al. | 71/90 |
| 3,856,503 | 12/1974 | Cebalo | 71/90 |

OTHER PUBLICATIONS

Kubo et al., J. Agr. Food Chem., 18 No. 1, 1/70, pp. 60–65.

*Primary Examiner*—Glennon H. Hollrah
*Attorney, Agent, or Firm*—Carl A. Cline

[57] ABSTRACT

A class of 5-ureido and thioureido-1,3,4-thiadiazole-2-sulfonamides bearing various substituents on both sulfonamide and ureido nitrogen atoms is employed to combat unwanted vegetation both pre- and post-emergently.

1 Claim, No Drawings

COMBATING UNWANTED VEGETATION WITH 1,3,4-THIADIAZOLE-2-SULFONAMIDES

DESCRIPTION OF THE INVENTION

A new class of highly phytotoxic substances has been discovered which may be applied to the locus of unwanted vegetation to effect control, either pre- or post-emergently. Effective compounds have the structural formula

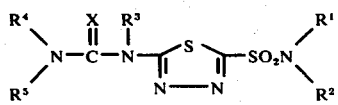

in which $R^1$ and $R^2$ are selected from hydrogen, lower cycloalkyl, lower alkyl, alkoxy, cyanoalkyl, aralkyl, alkoxyalkyl, alkylaminoalkyl, lower alkenyl and lower alkynyl substituents and heterocyclic structures in which $R^1$ and $R^2$ are together alkylene or oxyalkylene with two to five carbon atoms, $R^3$ is hydrogen, methyl or ethyl, $R^4$ is hydrogen or lower alkyl, $R^5$ is selected from lower alkyl, lower alkenyl and lower cycloalkyl substituents and X is oxygen or sulfur. In the preferred embodiment of the method a phytotoxic agricultural composition is prepared for use, comprising an effective amount of a compound as defined above, in combination with a major amount of an efficient organic solvent and a minor amount of a surface active agent, sufficient to disperse the composition in water. The most useful efficient solvents generally are mixtures of industrial solvents, usually selected from hydrocarbon, ketone and ester types, mixtures being more economical and efficient than individual substances. Both solvents and surface active agents are conveniently selected from those which are approved for agricultural use by the proper regulating agencies. Specific solvents which are useful in the preparation of the preferred type of agricultural compositions are toluene, xylene, isophorone, cyclohexanone, mesityl oxide and ethyl acetate. Blends of anionic and nonionic surfactants have proved to be particularly desirable as dispersing agents.

Specific compounds which are illustrative of the class of herbicides are listed in Table 1.

TABLE I

| COMPOUND NO. | $R^1$ | $R^2$ | $R^3$ | $R^4$ | $R^5$ | M.P. | X |
|---|---|---|---|---|---|---|---|
| 1 | $C_2H_5$ | $C_2H_5$ | $CH_3$ | H | $CH_3$ | 208.0–209.5 | O |
| 2 | H | $CH_3$ | H | H | $CH_3$ | 227–8 | O |
| 3 | H | $C_2H_5$ | H | H | $CH_3$ | 199–200 | O |
| 4 | H | $iC_3H_7$ | H | H | $CH_3$ | 183–6 | O |
| 5 | H | $nC_4H_9$ | H | H | $CH_3$ | 183–5 | O |
| 6 | H | $-CH_2CH=CH_2$ | H | H | $CH_3$ | 193–194.5 | O |
| 7 | H | $tC_4H_9$ | H | H | $CH_3$ | 245–6 (dec) | O |
| 8 | H | $cycloC_3H_5$ | H | H | $CH_3$ | 181–3 | O |
| 9 | H | $C_6H_5CH_2$ | H | H | $CH_3$ | 175–8 | O |
| 10 | $C_2H_5$ | $C_2H_5$ | H | H | $CH_3$ | 168–9 | O |
| 11 | $nC_3H_7$ | $nC_3H_7$ | H | H | $CH_3$ | 144–6 | O |
| 12 | $nC_4H_9$ | $nC_4H_9$ | H | H | $CH_3$ | 146–8 | O |
| 13 | $isoC_4H_9$ | $isoC_4H_9$ | H | H | $CH_3$ | 174–5 | O |
| 14 | $C_2H_5$ | $nC_4H_9$ | H | H | $CH_3$ | 177–9 | O |
| 15 | ($R^1,R^2=-CH_2CH_2OCH_2CH_2-$) | | H | H | $CH_3$ | 229–3 | O |
| 16 | $iC_3H_7$ | $C_6H_5CH_2-$ | H | H | $CH_3$ | 165–8 | O |
| 17 | H | $C_6H_5$ | H | H | $CH_3$ | 189–90 | O |
| 18 | $C_2H_5$ | $C_2H_5$ | $CH_3$ | H | $C_2H_5$ | 178–80 | O |
| 19 | $C_2H_5$ | $C_2H_5$ | $CH_3$ | H | $iC_3H_7$ | 84.0–86.5 | O |
| 20 | $C_2H_5$ | $C_2H_5$ | $CH_3$ | H | $nC_3H_7$ | 115–6 | O |
| 21 | $C_2H_5$ | $C_2H_5$ | $CH_3$ | H | $C_6H_5$ | 126–8 | O |
| 22 | $C_2H_5$ | $C_2H_5$ | $CH_3$ | H | $-CH_2-CH=CH_2$ | 107–8 | O |
| 23 | $C_2H_5$ | $C_2H_5$ | $CH_3$ | H | $CH_3$ | 130–1 | S |
| 24 | H | H | H | H | $CH_3$ | >310 | O |
| 25 | $-CH_2CH=CH_2$ | $-CH_2CH=CH_2$ | H | H | $CH_3$ | 134–5 | O |
| 26 | H | $-CH_2C\equiv CH$ | H | H | $CH_3$ | 179–82 | O |
| 27 | $-CH_2C\equiv CH$ | $-CH_2C\equiv CH$ | H | H | $CH_3$ | 191–3 | O |
| 28 | H | $nC_3H_7$ | H | H | $CH_3$ | 169–71 | O |
| 29 | $CH_3$ | $-CH_2CH_2CN$ | H | H | $CH_3$ | 168–71 | O |
| 30 | $C_2H_5$ | $C_2H_5$ | $CH_3$ | H | $cycloC_6H_{11}$ | 114–115.5 | O |
| 31 | $C_2H_5$ | $C_2H_5$ | $CH_3$ | $CH_3$ | $CH_3$ | 63–5 | O |
| 32 | H | $iC_3H_7$ | $CH_3$ | H | $CH_3$ | 197–9 | O |
| 33 | $CH_3$ | $CH_3$ | H | H | $CH_3$ | 193–6 | O |
| 34 | H | $CH_3$ | $CH_3$ | H | $CH_3$ | 158–60 | O |
| 35 | H | $-CH_2CH=CH_2$ | $CH_3$ | H | $CH_3$ | 145–7 | O |
| 36 | H | $cyclo\ C_3H_5$ | $CH_3$ | H | $CH_3$ | 193–5 | O |
| 37 | $CH_3$ | $CH_3$ | $CH_3$ | H | $CH_3$ | 211–14 | O |
| 38 | H | $CH_2C_6H_5$ | $CH_3$ | H | $CH_3$ | oil | O |
| 39 | $-CH_2CH=CH_2$ | $-CH_2CH=CH_2$ | $CH_3$ | H | $CH_3$ | 109–11 | O |
| 40 | $CH_3$ | $CH_3$ | $C_2H_5$ | H | $CH_3$ | 145–148.5 | O |
| 41 | H | ![benzyl-Cl] | $CH_3$ | H | $CH_3$ | 123–4 | O |
| 42 | $CH_3$ | $CH_3$ | $CH_3$ | $CH_3$ | $CH_3$ | 89–91 | O |
| 43 | H | $cyclo\ C_3H_5$ | $C_2H_5$ | H | $-CH_2CH=CH_2$ | 155–7 | O |

TABLE I-continued

| COMPOUND NO. | $R^1$ | $R^2$ | $R^3$ | $R^4$ | $R^5$ | M.P. | X |
|---|---|---|---|---|---|---|---|
| 44 | $CH_3$ | $CH_3$ | $C_2H_5$ | $CH_3$ | $CH_3$ | 71–2 | O |
| 45 | H | cyclo $C_3H_5$ | $C_2H_5$ | H | $CH_3$ | 83.5–84.5 | O |
| 46 | H | $C_{18}H_{37}$ | $CH_3$ | H | $CH_3$ | 118–130 | O |
| 47 | H | $-CH_2CH_2OH$ | $CH_3$ | H | $CH_3$ | 187–9 | O |
| 48 | ($R^1,R^2 = -CH_2CH_2CH_2CH_2-$) | | $CH_3$ | H | $CH_3$ | 220–4 | O |
| 49 | H | $-CH_2CH_2CH_2OCH_3$ | $CH_3$ | H | $CH_3$ | 91–3 | O |
| 50 | H | $-CH_2CH_2N(C_2H_5)_2$ | $CH_3$ | H | $CH_3$ | 89–92 | O |

Several general methods may be used to prepare the compounds listed in Table 1.

For all those (I) where $R^3=H$ (compound Nos. 2–17 and 24–29) and some where $R^3=CH_3$ (compound Nos. 32–39, 41 and 46–50) the route shown in Scheme A was used, starting with the known 2-amino-5-mercapto-1,3,4-thiadiazoles (IVa and IVb)

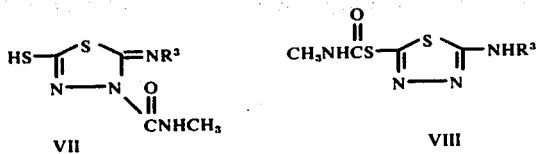

VII   VIII

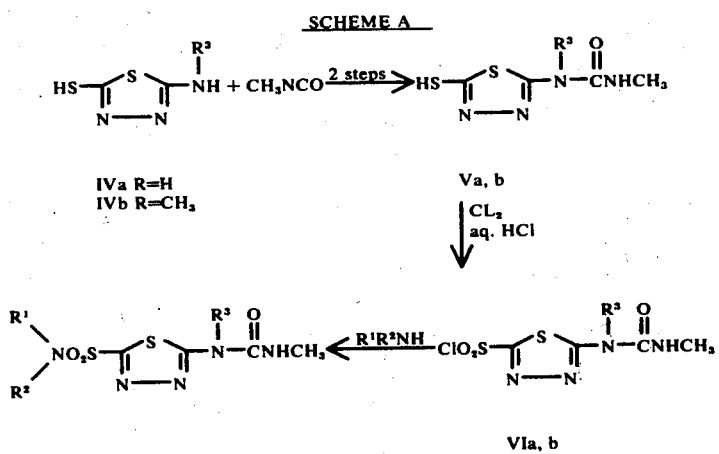

In the reaction of IVa and IVb with methyl isocyanate using either benzene or dioxane as solvent, the product obtained did not have structure V (a or b), but was an isomer or mixture of isomers. In the case of the product for IVa, conversion to Va could be accomplished by either recrystallizing from ethanol or methanol or by warming slightly in dimethyl sulfoxide solution. While these methods were ineffective when $R^3=CH_3$, Vb was obtained in good yield by heating the initial IVb methyl isocyanate reaction product with triethylamine.

The structures of the isomeric precursors to Va and Vb have not been determined but the more likely possibilities are VII, VIII and IX.

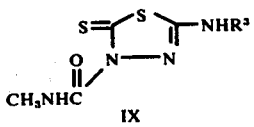

Chlorination of a suspension of Va or Vb in dilute hydrochloric acid gave, in good yield, the sulfonyl chloride (VI) which reacted smoothly with ammonia and amines to give the sulfonamides.

The preparation of the remainder of those (I) where $R^3=CH_3$ or $C_2H_5$ was according to Scheme B.

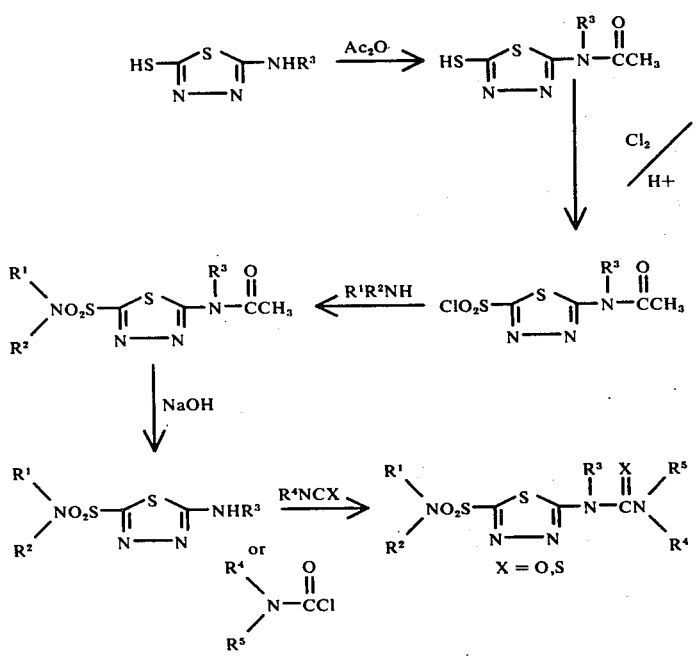

Preparation of N-Methyl-N'-(5-mercapto-1,3,4-thiadiazol-2-yl)urea

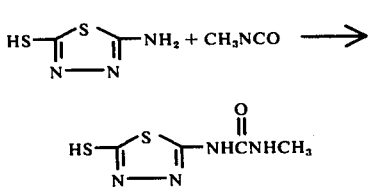

To a suspension of 10.5 g of 2-amino-5-mercapto-1,3,4-thiadiazole in 100 ml of benzene is added 4.5 g of methyl isocyanate and the mixture is stirred overnight at room temperature. The solid is collected by filtration, dried and dissolved in the minimum quantity of dimethyl sulfoxide by warming slightly. Dilution of this solution with water gives 13.0 g of N-methyl-N'-(5-mercapto-1,3,4-thiadiazol-2-yl)urea. A sample recrystallized from ethanol melted at 230°–232° with decomposition.

Preparation of N-Methyl-N'-(5-chlorosulfonyl-1,3,4-thiadiazol-2-yl)urea

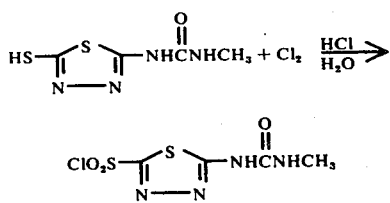

Chlorine gas is bubbled rapidly at 0°–7° through a stirred suspension of 8.0 g. of N-methyl-N'-(5-mercapto-1,3,4-thiadiazol-2-yl) urea in 200 ml. of 10% hydrochloric acid. After 1-2 hours, the mixture appears saturated with excess chlorine and the solid present is collected by filtration and washed with water to give 10.5 g of N-Methyl-N'-(5-chlorosulfonyl-1,3,4-thiadiazol-2-yl) urea m.p. 155° (dec.).

Preparation of N,N'-Dimethyl-N'-(5-Mercapto-1,3,4-thiadiazol-2-yl) urea

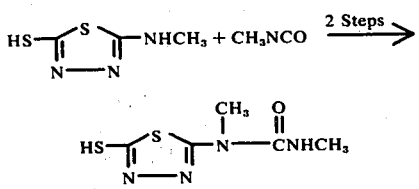

To a stirred slurry of 126 g of 2-methyl-amino-5-mercapto-1,3,4-thiadiazole in 525 ml of dioxane containing a few drops of triethylamine is added 49 g of methyl isocyanate. After stirring two hours at room temperature, the solid is collected by filtration and washed with hexane giving 165 g, melting at 162°–3°. This product is heated on the steam bath 1 ½–2 hours with 250 ml of triethylamine, during which time the initial solid is converted to a heavy amber oil. The supernatent liquid is decanted and the oil is dissolved in water and neutralized with dilute hydrochloric acid to pH 2–3. The precipitated solid is collected and washed with water and air dried, giving 132 g of N,N'-dimethyl-N'-(5-mercapto-1,3,4-thiadiazol-2-yl)urea, m.p. 230° (dec.).

Preparation of N,N'-Dimethyl-N'-(5-chlorosulfonyl-1,3,4-thiadiazol-2-yl)urea

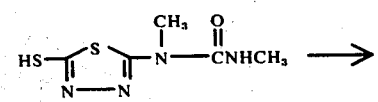

-continued

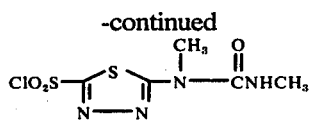

Chlorine gas is bubbled rapidly through a suspension of 20 g of N,N'-dimethyl-N'-(5-mercapto-1,3,4-thiadiazol-2-yl) urea in 300 ml of 10% hydrochloric acid. When the mixture is saturated with chlorine, the solid is filtered, washed with water and air dried to give 22.8 g of N,N'-dimethyl-N'-(5-chlorosulfonyl-1,3,4-thiadiazol-2-yl)urea, m.p. 95° (dec.).

Preparation of 2-(N'-Methylcarbamido) or (N,N'-Dimethylcarbamido)-1,3,4-thiadiazole-5-sulfonamides

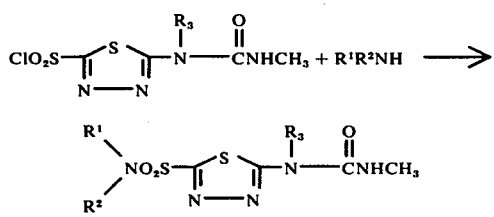

The sulfonamides (Nos. 2–17, 24–29, 32–39 and 41) listed in Table I, where $R^3$=H or $CH_3$ were prepared by a general method illustrated by the following procedure To a stirred and cooled solution of 5.9 g of diisobutylamine in 30 ml of dioxane is added rapidly, in small portions, 5.9 g of N-methyl-N'-(5-chlorosulfonyl)-1,3,4-thiadiazol-2-yl)urea. After stirring one hour in the ice bath, the slurry is diluted 2-4 fold with water, giving 6.7 g of 2-(N-methyl-carbamido)-1,3,4-thiadiazole-5-N,N-diisobutylsulfonamide, m.p. 174°–5°.

Those sulfonamides (Nos. 1, 18–23, 30, 31, 40 and 43–45) listed in Table I in which $R^3$ is alkyl were prepared by general methods illustrated by the following procedures Preparation of 2-(N'-methylacetamido)-1,3,4-thiadiazole-5-sulfonamides Method A Diethylamine (36.5 g, 0.5 mol) in 50 ml acetone was chilled in an ice-water bath. To the stirred solution was added portionwise over a 30 min. period 2-(N'-methylacetamido)-1,3,4-thiadiazole-5-sulfonyl chloride (25.6 g 0.1 mol). After an additional 15 min. of stirring, the thick white suspension was poured onto 400 ml of ice-water containing 100 ml 10% HCl. The white solid was isolated by filtration and after washing several times with water was air dried affording 28 g (96%) of product, m.p. 148°–50°.

Method B

Procedure as in A except that p-dioxane was used in place of acetone. Reactants were used in the ratio of 30mmol of sulfonyl chloride: 60 mmol of amine: 30 ml of dioxane. The product was removed by filtration and a second crop obtained by diluting the filtrate with water affording a 91% yield, m.p. 152.5°–3.0°.

Preparation of 2-N'-Methylamino-1,3,4-thiadiazole-5-N,N-diethylsulfonamide

A suspension of 2-(N'-methylacetamido-1,3,4-thiadiazole-5-N,N-diethysulfonamide (23g, 0.8 mol) in 1 liter of 10% NaOH with sufficient ethanol to partially effect solution was stirred overnight at room temperature. Ice was added and the resulting white solid removed by filtration. Washing several times with cold water and drying on filter afforded 16 g (80%) of product, m.p. 129.0°–130.0°. Thin layer chromatography (Brinkmann silica gel: $CHCl_3$ with 10% acetone) indicated reaction complete after 4 hours.

Preparation of 5-(1,3-Dimethylureido)-N,N-diethyl-1,3,4-thiadiazole-2-sulfonamide To a stirred suspension of 2-N'-methylamino-1,3,4-thiadiazole-5-N,N-diethylsulfonamide (5 g, 20 mmol) in 30 ml p-dioxane was added dropwise at room temperature methyl isocyanate (1.2 g, 20 mmol). Stirred 1.5 hr and product removed by filtration affording 4.2 g (69%) product, m.p. 208.0°–9.5°. (Abs. EtOH)

Combating Unwanted Vegetation

The novel herbicides are effective when used both post- and pre-emergently. There is described below an illustrative procedure for herbicidal use of the compounds under controlled conditions in the greenhouse so as to obtain data on phytotoxic activity and selectivity.

1. Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The species of plants on which each compound was to be tested were planted in four-inch pots in a greenhouse. Ten to eighteen days after emergence of the plants, three pots of each species were sprayed with an aqueous dispersion of the active compound prepared as described above, at a rate of 5 lb of active compound per acre and at a spray volume of 60 gallons per acre. Approximately one week after the spray application the plants were observed and the results rated according to the following schedule.

DEGREE OF EFFECT

0 = no effect
1 = slight effect
2 = moderate effect
3 = severe effect
4 = maximum effect (all plants died.

The same rating schedule was employed to judge pre-emergent results obtained according to the procedure below.

2. Pre-Emergent Use

A solution of each active compound was prepared by dissolving 290 mg of the compound to be tested in 200 ml of acetone. Disposable expanded polystyrene trays about 2 ½ inches deep and about one square foot in area were prepared and seeded with the acetone solution at the rate of 10 lb of active chemical per acre of sprayed area and were then covered with about ¼ inch of soil. One group of trays, which had been seeded with alfalfa, brome, flax, oats, radishes and sugar beets were held at 75° F day temperature; another set of trays seeded with corn, coxcomb, cotton, crabgrass, millet and soybeans was held at 85° F. Twenty-one days after seeding and treatment the plantings were examined and herbicidal effect was rated according to the above schedule.

Both post-emergent and pre-emergent results are set forth in Table II.

TABLE II

| COMPOUND NO. | USE TYPE | Crabgrass | Coxcomb | Brome | Millet | Alfalfa | Oats | Radish | Sugar Beet | Tomato |
|---|---|---|---|---|---|---|---|---|---|---|
| 1 | Post | | | | 4 | 4 | 4 | 4 | 4 | 4 |
|   | Pre | 4 | 4 | 4 | 4 | — | — | 4 | 4 | |
| 2 | Post | | | | 4 | 4 | 4 | 4 | 4 | 4 |
|   | Pre | 4 | 4 | 4 | 4 | — | — | 4 | 4 | |
| 3 | Post | | | | 4 | 4 | 4 | 4 | 4 | 4 |
|   | Pre | 4 | 4 | 4 | 4 | — | — | 4 | 4 | |
| 4 | Post | | | | 4 | 4 | 4 | 4 | 4 | 4 |
|   | Pre | 4 | 4 | 4 | 4 | — | — | 4 | 4 | |
| 5 | Post | | | | 3 | 4 | 3 | 4 | 4 | 4 |
|   | Pre | 2 | 3 | 3 | 3 | — | — | 4 | 4 | |
| 6 | Post | | | | 4 | 4 | 4 | 4 | 4 | 4 |
|   | Pre | 3 | 3 | 4 | 4 | — | — | 4 | 4 | |
| 7 | Post | | | | 0 | 4 | 0 | 2 | 4 | 3 |
|   | Pre | 2 | 4 | 3 | 2 | — | — | 4 | 4 | |
| 8 | Post | | | | 4 | 4 | 4 | 4 | 4 | 4 |
|   | Pre | 3 | 4 | 4 | 4 | — | — | 4 | 4 | |
| 9 | Post | | | | 3 | 4 | 2 | 4 | 4 | 4 |
|   | Pre | 1 | 2 | 2 | 1 | | | 2 | 2 | |
| 10 | Post | | | | 4 | 4 | 4 | 4 | 4 | 4 |
|    | Pre | 4 | 4 | 4 | 4 | — | — | 4 | 4 | |
| 11 | Post | | | | 3 | 4 | 2 | 4 | 4 | 4 |
|    | Pre | 2 | 4 | 4 | 3 | — | — | 4 | 4 | |
| 12 | Post | | | | 1 | 4 | 1 | 4 | 4 | 4 |
|    | Pre | 0 | 2 | 0 | 0 | — | — | 1 | 2 | |
| 13 | Post | | | | 3 | 4 | 1 | 4 | 4 | 4 |
|    | Pre | 1 | 4 | 2 | 1 | | | 2 | 4 | |
| 14 | Post | | | | 4 | 4 | 3 | 4 | 4 | 4 |
|    | Pre | 1 | 3 | 4 | 3 | | | 4 | 4 | |
| 15 | Post | | | | 4 | 4 | 4 | 4 | 4 | 4 |
|    | Pre | 3 | 4 | 4 | 4 | | | 4 | 4 | |
| 16 | Post | | | | 3 | 4 | 1 | 4 | 4 | 4 |
|    | Pre | 1 | 3 | 4 | 0 | | | 4 | 4 | |
| 17 | Post | | | | 0 | 1 | 0 | 1 | 3 | 2 |
|    | Pre | 0 | 3 | 0 | 1 | | | 1 | 3 | |
| 18 | Post | | | | 3 | 4 | 3 | 4 | 4 | 4 |
|    | Pre | 4 | 4 | 4 | 4 | | | 4 | 4 | |
| 19 | Post | | | | 1 | 3 | 2 | 4 | 4 | 4 |
|    | Pre | 2 | 4 | 4 | 4 | | | 4 | 4 | |
| 20 | Post | | | | 1 | 4 | 1 | 3 | 4 | 3 |
|    | Pre | 1 | 4 | 3 | 3 | | | 4 | 4 | |
| 21 | Post | | | | 0 | 0 | 0 | 0 | 0 | 0 |
|    | Pre | 1 | 3 | 1 | 1 | | | 1 | 1 | |
| 22 | Post | | | | 4 | 4 | 4 | 4 | 4 | 4 |
|    | Pre | 2 | 4 | 4 | 4 | | | 4 | 4 | |
| 23 | Post | | | | 1 | 3 | 1 | 4 | 4 | 3 |
|    | Pre | 2 | 4 | 3 | 3 | | | 4 | 4 | |
| 24 | Post | | | | 0 | 1 | 0 | 1 | 3 | 4 |
|    | Pre | 0 | 0 | 1 | 0 | | | 0 | 1 | |
| 25 | Post | | | | 4 | 4 | 3 | 4 | 4 | 4 |
|    | Pre | 3 | 4 | 4 | 4 | | | 4 | 4 | |
| 26 | Post | | | | 4 | 4 | 4 | 4 | 4 | 4 |
|    | Pre | 3 | 4 | 4 | 4 | | | 4 | 4 | |
| 27 | Post | | | | 4 | 4 | 1 | 4 | 4 | 4 |
|    | Pre | 3 | 4 | 4 | 4 | | | 4 | 4 | |
| 28 | Post | | | | 4 | 4 | 4 | 4 | 4 | 4 |
|    | Pre | 4 | 4 | 4 | 4 | | | 4 | 4 | |
| 29 | Post | | | | 4 | 4 | 3 | 4 | 4 | 4 |
|    | Pre | 4 | 4 | 4 | 4 | | | 4 | 4 | |
| 30 | Post | | | | 1 | 0 | 0 | 2 | 1 | 1 |
|    | Pre | 0 | 1 | 0 | 0 | | | 1 | 1 | |
| 31 | Post | | | | 4 | 4 | 4 | 4 | 4 | 4 |
|    | Pre | 4 | 4 | 4 | 4 | | | 4 | 4 | |
| 32 | Post | | | | 4 | 4 | 4 | 4 | 4 | 4 |
|    | Pre | 3 | 4 | 4 | 4 | | | 4 | 4 | |
| 33 | Post | | | | 4 | 4 | 4 | 4 | 4 | 4 |
|    | Pre | 3 | 4 | 4 | 4 | | | 4 | 4 | |
| 34 | Post | | | | 4 | 4 | 4 | 4 | 4 | 4 |
|    | Pre | 3 | 4 | 4 | 4 | | | 4 | 4 | |
| 35 | Post | | | | 4 | 4 | 4 | 4 | 4 | 4 |
|    | Pre | 3 | 4 | 4 | 4 | | | 4 | 4 | |
| 36 | Post | | | | 4 | 4 | 4 | 4 | 4 | 4 |
|    | Pre | 2 | 4 | 2 | 3 | | | 2 | 4 | |
| 37 | Post | | | | 4 | 4 | 4 | 4 | 4 | 4 |
|    | Pre | 3 | 4 | 4 | 4 | | | 4 | 4 | |
| 38 | Post | | | | 4 | 4 | 3 | 4 | 4 | 4 |
|    | Pre | | | | | | | | | |
| 39 | Post | | | | 4 | 4 | 4 | 4 | 4 | 4 |
|    | Pre | | | | | | | | | |
| 40 | Post | | | | 4 | 4 | 4 | 4 | 4 | 4 |

TABLE II-continued

| COMPOUND NO. | USE TYPE | Crabgrass | Coxcomb | Brome | Millet | Alfalfa | Oats | Radish | Sugar Beet | Tomato |
|---|---|---|---|---|---|---|---|---|---|---|
| | Pre | | | | | | | | | |

In a further test of both pre and post-emergent use of illustrative compounds, twenty-four species of plants were treated. Although there were in several instances fairly severe effects on soybeans, peanuts, cotton, corn and grain sorghum some of the compounds killed a number of plant species in the presence of these crop plants. Results are presented in Table III. The ratings were all made according to the schedule disclosed above.

TABLE III

COMPOUND NO. 1

| MODE OF APPLICATION | PRE 3 lb/A | PRE 1 lb/A | POST 3 lb/A | POST 1 lb/A |
|---|---|---|---|---|
| Plant Species | | | | |
| Cocklebur | 4 | 4 | *4 | *4 |
| Lambsquarter | 4 | 4 | 4 | 4 |
| Morning Glory | 4 | 4 | 4 | 2 |
| Pigweed | 4 | 4 | 4 | 4 |
| Wild Buckwheat | 4 | 4 | 4 | 4 |
| Wild Mustard | 4 | 4 | 4 | 3 |
| Barnyard Grass | 4 | 4 | 4 | 3 |
| Crabgrass | 4 | 4 | 4 | 3 |
| Downy Brome | 4 | 3 | 3 | 0 |
| Giant Foxtail | 4 | 4 | 4 | 1 |
| Green Foxtail | 4 | 4 | 4 | 2 |
| Nutsedge | 1 | 0 | 3 | 0 |
| Shattercane | 4 | 4 | 4 | 1 |
| Wild Oats | 4 | 4 | 4 | 1 |
| Alfalfa | 3 | 1 | 4 | 0 |
| Cotton | 4 | 3 | 4 | 4 |
| Peanut | 2 | 0 | 1 | 0 |
| Soybean | 4 | 4 | 4 | 3 |
| Sugar Beets | 4 | 4 | 4 | 3 |
| Tomato | 4 | 4 | 4 | 4 |
| Corn | 4 | 4 | 2 | 1 |
| Grain Sorghum | 4 | 4 | 3 | 0 |
| Rice | 4 | 4 | 4 | 1 |
| Wheat | 4 | 4 | 4 | 1 |

COMPOUND NO. 2

| Plant Species | | | | |
|---|---|---|---|---|
| Cocklebur | 0 | 0 | — | — |
| Lambsquarter | 4 | 1 | 4 | 4 |
| Morning Glory | 0 | 0 | 1 | 1 |
| Pigweed | 4 | 3 | 4 | 4 |
| Wild Buckwheat | 2 | 0 | 4 | 4 |
| Wild Mustard | 4 | 1 | 4 | 4 |
| Barnyard Grass | 4 | 3 | 4 | 4 |
| Crabgrass | 4 | 3 | 4 | 4 |
| Downy Brome | 3 | 0 | 3 | 1 |
| Giant Foxtail | 4 | 2 | 4 | 4 |
| Green Foxtail | 4 | 2 | 4 | 4 |
| Nutsedge | 0 | 0 | 0 | 0 |
| Shattercane | 4 | 3 | 4 | 3 |
| Wild Oats | 3 | 1 | 4 | 4 |
| Alfalfa | 3 | 1 | 4 | 4 |
| Cotton | 0 | 0 | 4 | 4 |
| Peanut | 0 | 0 | 2 | 1 |
| Soybean | 0 | 0 | 4 | 2 |
| Sugar Beets | 1 | 0 | 4 | 4 |
| Tomato | 4 | 1 | 4 | 4 |
| Corn | 3 | 2 | 2 | 1 |
| Grain Sorghum | 4 | 2 | 4 | 3 |
| Rice | 4 | 3 | 4 | 4 |
| Wheat | 4 | 3 | 4 | 4 |

COMPOUND NO. 3

| Plant Species | | | | |
|---|---|---|---|---|
| Cocklebur | 0 | 0 | *4 | *4 |
| Lambsquarter | 4 | 4 | 4 | 4 |
| Morning Glory | 0 | 0 | 2 | 1 |
| Pigweed | 4 | 4 | 4 | 4 |
| Wild Buckwheat | 0 | 0 | 4 | 4 |
| Wild Mustard | 4 | 1 | 4 | 4 |
| Barnyard Grass | 4 | 4 | 4 | 4 |
| Crabgrass | 4 | 4 | 4 | 4 |
| Downy Brome | 4 | 3 | 4 | 2 |
| Giant Foxtail | 4 | 4 | 4 | 3 |
| Green Foxtail | 4 | 4 | 4 | 4 |
| Nutsedge | 0 | 0 | 0 | 0 |
| Shattercane | 4 | 3 | 3 | 4 |
| Wild Oats | 4 | 4 | 4 | 4 |
| Alfalfa | 3 | 1 | 4 | 3 |
| Cotton | 0 | 0 | 1 | 0 |
| Peanut | 0 | 0 | 3 | 3 |
| Soybean | 0 | 0 | 4 | 4 |
| Sugar Beets | 4 | 4 | 4 | 4 |
| Tomato | 4 | 3 | 4 | 4 |
| Corn | 4 | 2 | 2 | 1 |
| Grain Sorghum | 4 | 3 | 4 | 2 |
| Rice | 4 | 4 | 3 | 1 |
| Wheat | 4 | 4 | 4 | 3 |

COMPOUND NO. 4

| Plant Species | | | | |
|---|---|---|---|---|
| Cocklebur | 0 | 0 | *4 | *4 |
| Lambsquarter | 4 | 4 | 4 | 1 |
| Morning Glory | 0 | 0 | 3 | 1 |
| Pigweed | 4 | 4 | 4 | 4 |
| Wild Buckwheat | 0 | 0 | 4 | 4 |
| Wild Mustard | 1 | 0 | 4 | 2 |
| Barnyard Grass | 3 | 2 | 3 | 3 |
| Crabgrass | 4 | 3 | 4 | 1 |
| Downy Brome | 4 | 3 | 3 | 2 |
| Giant Foxtail | 4 | 2 | 4 | 1 |
| Green Foxtail | 2 | 0 | 3 | 1 |
| Nutsedge | 0 | 0 | 1 | 0 |
| Shattercane | 3 | 0 | 3 | 0 |
| Wild Oats | 4 | 1 | 3 | 0 |
| Alfalfa | 1 | 0 | 4 | 2 |
| Cotton | 0 | 0 | 3 | 0 |
| Peanut | 0 | 0 | 1 | 1 |
| Soybean | 2 | 0 | 4 | 2 |
| Sugar Beets | 4 | 2 | 4 | 4 |
| Tomato | 4 | 0 | 4 | 4 |
| Corn | 2 | 0 | 2 | 0 |
| Grain Sorghum | 3 | 0 | 1 | 0 |
| Rice | 3 | 2 | 3 | 1 |
| Wheat | 4 | 2 | 2 | 0 |

COMPOUND NO. 5

| Plant Species | | | | |
|---|---|---|---|---|
| Cocklebur | 0 | 0 | *3 | *1 |
| Lambsquarter | 4 | 4 | 4 | 4 |
| Morning Glory | 0 | 0 | 2 | 1 |
| Pigweed | 4 | 4 | 4 | 4 |
| Wild Buckwheat | 1 | 0 | 4 | 3 |
| Wild Mustard | 4 | 0 | 4 | 4 |
| Barnyard Grass | 3 | 2 | 3 | 3 |
| Crabgrass | 3 | 3 | 4 | 3 |
| Downy Brome | 3 | 1 | 2 | 1 |
| Giant Foxtail | 3 | 2 | 3 | 2 |
| Green Foxtail | 2 | 1 | 4 | 2 |
| Nutsedge | 0 | 0 | 0 | 0 |
| Shattercane | 1 | 0 | 2 | 0 |
| Wild Oats | 3 | 2 | 3 | 1 |
| Alfalfa | 1 | 0 | 4 | 3 |
| Cotton | 0 | 0 | 3 | 0 |
| Peanut | 0 | 0 | 1 | 0 |
| Soybean | 1 | 0 | 3 | 3 |
| Sugar Beets | 4 | 1 | 4 | 3 |
| Tomato | 4 | 0 | 4 | 4 |
| Corn | 1 | 0 | 2 | 0 |
| Grain Sorghum | 1 | 0 | 2 | 0 |
| Rice | 3 | 2 | 2 | 1 |
| Wheat | 4 | 3 | 2 | 1 |

COMPOUND NO. 6

| Plant Species | | | | |
|---|---|---|---|---|
| Cocklebur | 0 | 0 | *4 | *4 |
| Lambsquarter | 4 | 4 | 4 | 4 |
| Morning Glory | 0 | 0 | 1 | 1 |
| Pigweed | 4 | 4 | 4 | 4 |
| Wild Buckwheat | 2 | 1 | 4 | 4 |
| Wild Mustard | 3 | 0 | 4 | 1 |
| Barnyard Grass | 4 | 3 | 4 | 3 |
| Crabgrass | 4 | 3 | 4 | 3 |
| Downy Brome | 4 | 3 | 3 | 1 |

TABLE III-continued

| | | | | |
|---|---|---|---|---|
| Giant Foxtail | 4 | 3 | 4 | 2 |
| Green Foxtail | 3 | 1 | 4 | 1 |
| Nutsedge | 0 | 0 | 0 | 0 |
| Shattercane | 3 | 1 | 2 | 0 |
| Wild Oats | 4 | 2 | 3 | 1 |
| Alfalfa | 1 | 0 | 3 | 2 |
| Cotton | 0 | 0 | 3 | 1 |
| Peanut | 0 | 0 | 1 | 0 |
| Soybean | 2 | 0 | 2 | 2 |
| Sugar Beets | 4 | 1 | 4 | 3 |
| Tomato | 4 | 3 | 4 | 4 |
| Corn | 4 | 1 | 2 | 1 |
| Grain Sorghum | 3 | 1 | 2 | 0 |
| Rice | 4 | 3 | 3 | 1 |
| Wheat | 4 | 4 | 3 | 1 |

COMPOUND NO. 7

| | | | | |
|---|---|---|---|---|
| Plant Species | | | | |
| Cocklebur | 0 | 0 | *0 | *0 |
| Lambsquarter | 3 | 1 | 1 | 0 |
| Morning Glory | 0 | 0 | 0 | 0 |
| Pigweed | 4 | 2 | 1 | 0 |
| Wild Buckwheat | 0 | 0 | 1 | 0 |
| Wild Mustard | 0 | 0 | 2 | 0 |
| Barnyard Grass | 2 | 0 | 0 | 0 |
| Crabgrass | 3 | 0 | 0 | 0 |
| Downy Brome | 1 | 0 | 0 | 0 |
| Giant Foxtail | 2 | 0 | 0 | 0 |
| Green Foxtail | 1 | 0 | 0 | 0 |
| Nutsedge | 0 | 0 | 0 | 0 |
| Shattercane | 0 | 0 | 0 | 0 |
| Wild Oats | 0 | 0 | 0 | 0 |
| Alfalfa | 0 | 0 | 0 | 0 |
| Cotton | 0 | 0 | 0 | 0 |
| Peanut | 0 | 0 | 0 | 0 |
| Soybean | 0 | 0 | 1 | 1 |
| Sugar Beets | 4 | 0 | 2 | 1 |
| Tomato | 1 | 1 | 2 | 1 |
| Corn | 0 | 0 | 0 | 0 |
| Grain Sorghum | 0 | 0 | 0 | 0 |
| Rice | 1 | 0 | 0 | 0 |
| Wheat | 1 | 0 | 0 | 0 |

COMPOUND NO. 10

| | | | | |
|---|---|---|---|---|
| Plant Species | | | | |
| Cocklebur | 0 | 0 | 4 | 4 |
| Lambsquarter | 4 | 3 | 4 | 4 |
| Morning Glory | 0 | 0 | 3 | 2 |
| Pigweed | 4 | 4 | 4 | 4 |
| Wild Buckwheat | 1 | 0 | 4 | 4 |
| Wild Mustard | 4 | 4 | 4 | 4 |
| Barnyard Grass | 4 | 4 | 4 | 3 |
| Crabgrass | 4 | 3 | 4 | 4 |
| Downy Brome | 1 | 0 | 3 | 2 |
| Giant Foxtail | 4 | 2 | 4 | 4 |
| Green Foxtail | 4 | 4 | 4 | 4 |
| Nutsedge | 0 | 0 | 0 | 0 |
| Shattercane | 4 | 4 | 4 | 3 |
| Wild Oats | 3 | 0 | 4 | 3 |
| Alfalfa | 4 | 2 | 4 | 4 |
| Cotton | 1 | 0 | 4 | 4 |
| Peanut | 0 | 0 | 2 | 1 |
| Soybean | 1 | 0 | 4 | 4 |
| Sugar Beets | 4 | 3 | 4 | 4 |
| Tomato | 4 | 1 | 4 | 4 |
| Corn | 2 | 1 | 1 | 1 |
| Grain Sorghum | 4 | 3 | 4 | 2 |
| Rice | 3 | 3 | 4 | 2 |
| Wheat | 4 | 1 | 4 | 3 |

COMPOUND NO. 11

| | | | | |
|---|---|---|---|---|
| Plant Species | | | | |
| Cocklebur | 0 | 0 | *2 | *0 |
| Lambsquarter | 4 | 2 | 4 | 4 |
| Morning Glory | 0 | 0 | 1 | 0 |
| Pigweed | 4 | 4 | 4 | 4 |
| Wild Buckwheat | 0 | 0 | 4 | 4 |
| Wild Mustard | 0 | 0 | 4 | 4 |
| Barnyard Grass | 0 | 0 | 2 | 1 |
| Crabgrass | 1 | 0 | 2 | 1 |
| Downy Brome | 0 | 0 | 1 | 0 |
| Giant Foxtail | 0 | 0 | 2 | 1 |
| Green Foxtail | 0 | 0 | 1 | 0 |
| Nutsedge | 0 | 0 | 0 | 0 |
| Shattercane | 0 | 0 | 0 | 0 |
| Wild Oats | 1 | 0 | 1 | 0 |
| Alfalfa | 0 | 0 | 4 | 3 |
| Cotton | 0 | 0 | 3 | 3 |
| Peanut | 0 | 0 | 1 | 0 |
| Soybean | 0 | 0 | 4 | 1 |
| Sugar Beets | 1 | 0 | 4 | 4 |
| Tomato | 0 | 0 | 4 | 4 |
| Corn | 0 | 0 | 0 | 0 |
| Grain Sorghum | 0 | 0 | 0 | 0 |
| Rice | 2 | 0 | 1 | 0 |
| Wheat | 3 | 0 | 1 | 0 |

COMPOUND NO. 12

| | | |
|---|---|---|
| Plant Species | | |
| Cocklebur | *1 | *0 |
| Lambsquarter | 2 | 1 |
| Morning Glory | 1 | 0 |
| Pigweed | 1 | 1 |
| Wild Buckwheat | 4 | 4 |
| Wild Mustard | 4 | 4 |
| Barnyard Grass | 0 | 0 |
| Crabgrass | 2 | 0 |
| Downy Brome | 2 | 0 |
| Giant Foxtail | 2 | 0 |
| Green Foxtail | 0 | 0 |
| Nutsedge | 0 | 0 |
| Shattercane | 0 | 0 |
| Wild Oats | 2 | 1 |
| Alfalfa | 2 | 1 |
| Cotton | 4 | 1 |
| Peanut | 1 | 0 |
| Soybean | 1 | 1 |
| Sugar Beets | 4 | 4 |
| Tomato | 4 | 2 |
| Corn | 0 | 0 |
| Grain Sorghum | 0 | 0 |
| Rice | 1 | 0 |
| Wheat | 0 | 0 |

0 = No injury
*Sunflower used in place of Cocklebur
4 = Complete Kill
— = No plants

We claim:
1. The method of combating unwanted vegetation comprising applying to the locus of the unwanted vegetation an effective amount of 5-(1,3,3-trimethylureido)-N,N-dimethyl-1,3,4-thiadiazole-2-sulfonamide.

* * * * *